United States Patent
Yang et al.

(10) Patent No.: US 9,482,631 B2
(45) Date of Patent: Nov. 1, 2016

(54) FORMATION CORE SAMPLE HOLDER ASSEMBLY AND TESTING METHOD FOR NUCLEAR MAGNETIC RESONANCE MEASUREMENTS

(71) Applicants: Zheng Yang, Richmond, CA (US); Boqin Sun, Danville, CA (US); John S. Zintsmaster, San Rafael, CA (US); Gerald Latorraca, Danville, CA (US); Ajit R. Pradhan, Walnut Creek, CA (US)

(72) Inventors: Zheng Yang, Richmond, CA (US); Boqin Sun, Danville, CA (US); John S. Zintsmaster, San Rafael, CA (US); Gerald Latorraca, Danville, CA (US); Ajit R. Pradhan, Walnut Creek, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 751 days.

(21) Appl. No.: 13/894,150

(22) Filed: May 14, 2013

(65) Prior Publication Data
US 2014/0340082 A1 Nov. 20, 2014

(51) Int. Cl.
| | |
|---|---|
| *G01N 24/08* | (2006.01) |
| *G01R 33/30* | (2006.01) |
| *G01V 3/14* | (2006.01) |
| *G01R 33/44* | (2006.01) |
| *G01V 3/32* | (2006.01) |

(52) U.S. Cl.
CPC ........... *G01N 24/081* (2013.01); *G01R 33/305* (2013.01); *G01V 3/14* (2013.01); *G01R 33/448* (2013.01); *G01V 3/32* (2013.01)

(58) Field of Classification Search
CPC .... G01R 33/305; G01R 33/448; G01V 3/14; G01V 3/32; G01N 24/081
See application file for complete search history.

(56) References Cited

U.S. PATENT DOCUMENTS

| | | | |
|---|---|---|---|
| 4,827,761 A | 5/1989 | Vinegar et al. | |
| 6,070,662 A | 6/2000 | Ciglenec et al. | |

(Continued)

FOREIGN PATENT DOCUMENTS

| | | |
|---|---|---|
| CN | 102062742 | 5/2011 |
| GB | 2489005 | 9/2012 |

(Continued)

OTHER PUBLICATIONS

Godefroy, S., et al.; "Temperature Effect on NMR Surface Relaxation in Rocks for Well Logging Applications"; J. Phys. Chem. B. 2002, vol. 106, pp. 11183-11190, XP-002729750.

(Continued)

*Primary Examiner* — Dixomara Vargas

(57) ABSTRACT

A core sample holder assembly for performing a laboratory magnetic resonance measurement of a core sample taken from a hydrocarbon containing formation is provided. The assembly comprises a pressure chamber provided by a hull and one or more flanges are sealingly coupled with the hull. A flexible core sample holder sleeve is arranged within the pressure chamber and is sealingly coupled with at least one of the flanges. An overburden fluid injection port is in fluid communication with an annular space between the hull and the flexible sleeve and is configured to inject overburden fluid into an annular space between the hull and the flexible sleeve. A pressure regulator is configured to maintain the overburden fluid in the annular space at an elevated pressure. A radio-frequency antenna, within the pressure chamber and wrapped around the sample holder sleeve, is configured to receive an electromagnetic-signal from the core sample. In use, the core sample is arranged substantially within the sleeve.

35 Claims, 8 Drawing Sheets

(56) References Cited

U.S. PATENT DOCUMENTS

| | | | |
|---|---|---|---|
| 6,114,851 A | 9/2000 | Kruspe et al. | |
| 6,429,653 B1 | 8/2002 | Kruspe et al. | |
| 6,492,809 B1 | 12/2002 | Speier et al. | |
| 6,559,640 B2 | 5/2003 | Taicher | |
| 6,583,621 B2 | 6/2003 | Prammer et al. | |
| 6,745,833 B2 | 6/2004 | Aronstam et al. | |
| 6,923,273 B2 * | 8/2005 | Terry | G01V 3/30 138/125 |
| 6,984,980 B2 | 1/2006 | Kruspe et al. | |
| 7,172,038 B2 * | 2/2007 | Terry | G01V 3/30 175/320 |
| 7,193,414 B2 | 3/2007 | Kruspe et al. | |
| 7,398,837 B2 | 7/2008 | Hall et al. | |
| 7,605,716 B2 | 10/2009 | Peter et al. | |
| 7,624,794 B2 | 12/2009 | Freedman et al. | |
| 7,683,613 B2 | 3/2010 | Freedman et al. | |
| 7,733,086 B2 | 6/2010 | Prammer et al. | |
| 7,931,784 B2 * | 4/2011 | Medoff | C10G 3/00 204/157.15 |
| 8,016,036 B2 | 9/2011 | Kirkwood et al. | |
| 8,236,535 B2 * | 8/2012 | Medoff | C07H 3/02 435/161 |
| 8,454,803 B2 * | 6/2013 | Medoff | C10G 3/00 204/157.15 |
| 8,518,683 B2 * | 8/2013 | Medoff | C07H 3/02 252/182.12 |
| 8,709,771 B2 * | 4/2014 | Medoff | C07H 3/02 435/135 |
| 8,747,624 B2 * | 6/2014 | Medoff | C10G 3/00 204/157.15 |
| 8,764,948 B2 * | 7/2014 | Medoff | C10G 3/00 204/157.63 |
| 8,771,480 B2 * | 7/2014 | Medoff | C10G 3/00 204/157.15 |
| 8,852,896 B2 * | 10/2014 | Medoff | C10G 3/00 204/165 |
| 9,023,183 B2 * | 5/2015 | Medoff | C10G 3/00 204/157.63 |
| 9,109,241 B2 * | 8/2015 | Medoff | C07H 3/02 |
| 9,138,715 B2 * | 9/2015 | Medoff | C10G 3/00 |
| 9,186,646 B2 * | 11/2015 | Medoff | C10G 3/00 |
| 9,290,780 B2 * | 3/2016 | Medoff | C07H 3/02 |
| 9,352,294 B1 * | 5/2016 | Medoff | C10G 3/00 |
| 2003/0155915 A1 | 8/2003 | Kruspe et al. | |
| 2004/0169511 A1 | 9/2004 | Minh et al. | |
| 2005/0030021 A1 | 2/2005 | Prammer et al. | |
| 2009/0256562 A1 | 10/2009 | Gao et al. | |
| 2009/0302847 A1 | 12/2009 | Knizhnik | |
| 2011/0050223 A1 | 3/2011 | Balcom et al. | |
| 2011/0198078 A1 | 8/2011 | Harrigan et al. | |
| 2011/0284231 A1 | 11/2011 | Becker | |
| 2012/0092016 A1 | 4/2012 | Kruspe | |
| 2012/0223235 A1 | 9/2012 | Maucec | |

FOREIGN PATENT DOCUMENTS

| | | |
|---|---|---|
| WO | 99/45234 A1 | 9/1999 |
| WO | 2011/133859 | 10/2011 |
| WO | 2012/068219 A2 | 5/2012 |

OTHER PUBLICATIONS

Han, H., et al.; "High Pressure Magnetic Resonance Imaging with Metallic Vessels"; Journal of Magnetic Resonance, 2011, vol. 213, pp. 90-97.

Mitchell, J., et al.; "Magnetic Resonance Imaging in Laboratory Petrophysical Core Analysis"; Physics Reports, 2013, vol. 526, pp. 165-225.

International Search Report, mailed Oct. 9, 2014, during the prosecution of International Application No. PCT/US2014/036600.

Written Opinion of the International Searching Authority, mailed Oct. 9, 2014, during the prosecution of International Application No. PCT/US2014/036600.

* cited by examiner

FORMATION CORE SAMPLE HOLDER ASSEMBLY AND TESTING METHOD FOR NUCLEAR MAGNETIC RESONANCE MEASUREMENTS

TECHNICAL FIELD

The disclosed embodiments relate generally to a formation core sample holder assembly and a core testing method. The disclosed embodiments relate specifically to a formation core holder for performing a nuclear magnetic resonance (NMR) experiment on a core sample at elevated temperature and pressure.

BACKGROUND

In the oil and gas production industry, it is common practice to perform one or more "in-situ" tests of a hydrocarbon containing or other formation using a logging probe operating within an exploration or production well. In some circumstances, these in-situ tests include one or more NMR measurements of the formation, including the rock and the fluid contained therein. Such measurements are useful in determining a $T_1$ value (the so-called "longitudinal relaxation time") and a $T_2$ value (the so-called "transverse relaxation time") associated with the formation (e.g., the rock and fluids within the rock) and a diffusion coefficient From $T_1$, $T_2$ and the diffusion coefficient, a wealth of information can be obtained about physical properties of the formation.

It is also common practice to take, while the exploration or production well is being drilled, one or more cylindrical core samples of the formation and to subsequently perform one or more laboratory tests with a core sample in a laboratory. In some circumstances, these laboratory tests include NMR measurements of the core sample. Measurements in the laboratory need to be representative of the in-situ measurements. Correct (i.e., representative) data are used to optimize and establish a recovery factor for the field. In particular, greater optimization of the recovery factor for certain enhanced oil recovery (EOR) processes is possible if representative laboratory data are available.

However, a gap exists between laboratory NMR measurements and in-situ NMR measurements because experimental apparatus for performing laboratory NMR measurements on a core sample are unable to reproduce reservoir conditions experienced by the in-situ logging probe during in-situ NMR measurements. In particular, a problem with core sample holder assemblies (e.g., laboratory assemblies) for NMR measurements is that they are not able to maintain the core sample at elevated temperature and pressure while NMR measurements are being taken.

Therefore, it is an objective of the present disclosure to provide a core holder assembly and core testing method, which provide a solution to these problems.

SUMMARY

One aspect of the present disclosure provides a core sample holder assembly for performing a laboratory nuclear magnetic resonance measurement of a core sample taken from a hydrocarbon containing formation is provided. The assembly comprises a pressure chamber provided by a hull and one or more flanges sealingly coupled to the hull. A flexible core sample holder sleeve is arranged within the pressure chamber and is sealingly coupled with at least one of the flanges. An overburden fluid injection port is in fluid communication with an annular space between the hull and the flexible sleeve and is configured to inject overburden fluid into an annular space between the hull and the flexible sleeve. A pressure regulator is configured to maintain the overburden fluid in the annular space at an elevated pressure. A radio-frequency antenna, within the pressure chamber and wrapped around the sample holder sleeve, is configured to receive an electromagnetic-signal from the core sample. In use, the core sample is arranged substantially within the sleeve.

Another aspect provides a core sample holder assembly for performing a laboratory magnetic resonance measurement of a core sample taken from a hydrocarbon containing formation. The core sample holder assembly comprises a pressure chamber provided by a hull and a pair of flanges arranged at opposite sides of the hull. A flexible core sample holder sleeve is arranged within the pressure chamber and is sealingly coupled with the pair of flanges. An overburden fluid injection port feeds through one of the flanges of the pair of flanges and is configured to inject overburden fluid into an annular space between the hull and the flexible sleeve. A pressure regulator is configured to maintain the overburden fluid in the annular space at a predetermined gauge pressure. A radio-frequency (RF) antenna is within the pressure chamber and is wrapped around the sample holder sleeve. The RF antenna is configured to receive an electromagnetic-signal from the core sample. In use, the core sample is arranged substantially within the sleeve.

In some embodiments, the apparatus further includes a heating element disposed on an outer surface of the pressure chamber. In some embodiments, the heating element is configured to heat the core sample to an elevated temperature in the range of about 200 degrees Fahrenheit to about 500 degrees Fahrenheit. In some embodiments, the heating element is configured to heat the core sample to an elevated temperature in the range of about room temperature to about 350 degrees Fahrenheit. In some embodiments, the apparatus further includes a thermocouple that is configured to monitor the elevated temperature of the core sample.

In some embodiments, the apparatus further includes a flooding fluid injection port fed through one of the flanges of the pair of flanges. This flooding fluid injection port is configured to inject a flooding fluid into the core sample. Further, a fluid outlet port feeds through the other flange of the pair of flanges. The fluid outlet port is configured for discharge of pore and/or injected fluid from the core sample.

In some embodiments, the apparatus further includes one or more electrical feedthroughs configured to electrically couple a first terminal and a second terminal of the RF antenna to external circuitry. In some embodiments, the applied gauge pressure that the outer sleeve is capable of withstanding is a pressure in a range between atmosphere to 7,500 psig. In some embodiments, the hull comprises stainless steel or titanium. In some embodiments, the flexible core sample holder sleeve comprises a non-magnetic plastic polymer, for example, one that is substantially free of hydrogen such as polytetrafluoroethylene.

Another aspect of the present disclosure provides a method of performing a laboratory nuclear magnetic resonance measurement of a core sample. The method comprises saturating the core sample with one or more fluids, the one or more fluids comprising at least one of a hydrocarbon-based fluid and a brine. While the core sample is saturated with the one or more fluids, a first pressure is applied to an exterior surface of a core sample, the core sample is heated to a first elevated temperature, and nuclear magnetic resonance (NMR) data is generated of the core sample and the one or more fluids at the first applied pressure and first elevated temperature. A value of one or more physical characteristics of the core sample is and the one or more fluids is determined as a function of the first applied pressure and the first elevated temperature. In some embodiments, the first elevated temperature is in a temperature range of about 200 degrees Fahrenheit to about 500 degrees Fahrenheit. In some embodiments, the first elevated temperature is in a temperature range of about room temperature to 350 Fahrenheit. In some embodiments, the first applied pressure is in a range between 0 psig to 7,500 psig.

In some embodiments, applying the pressure further comprises positioning the core sample substantially within a sleeve, where the sleeve comprises a respective material and where the sleeve is capable of transmitting, from an exterior surface of the sleeve to an interior surface of the sleeve, an applied pressure. The sleeve is surrounded with an overburden fluid and the overburden fluid is pressurized, thereby applying a pressure to the exterior surface of the sleeve. In some embodiments, the heating the core sample to the first elevated temperature further comprises heating the overburden fluid, thereby indirectly heating the core sample by using the overburden fluid as a heat-transfer medium. In some embodiments, the respective material comprises polytetrafluoroethylene or more generally is substantially free of hydrogen. In some embodiments, the overburden fluid is also substantially free of hydrogen, is electrically insulating, is a fluorocarbon-based fluid, and/or comprises a fluid having a chemical formula $C_xF_y$.

In some embodiments, the step of determining one or more physical characteristics of the core sample includes performing at least one of (i) typing hydrocarbons in the one or more fluids, (ii) estimating pore-size distributions of the core sample, (iii) evaluating a viscosity of the one or more fluids, (iv) determining a permeability of the core sample, and (vi) determining a wettability of the core sample.

In some embodiment the at least one characteristic of the core sample is determined under static conditions and is further determined under flooding conditions (e.g., while performing the generating operation, pumping at least one flooding fluid into the core sample). In some such embodiments, the at least one flooding fluid includes oil, water, brine, surfactant solution or a mixture thereof. In some such embodiments, the at least one flooding fluid includes a gas. In some embodiments, the gas includes carbon dioxide, nitrogen, methane, sulfur dioxide, nitrogen dioxide, or a mixture thereof.

In some embodiments, the method further includes generating a forward model for one or more wettability indices of the core sample.

In some embodiments, the method further comprises, while the core sample is saturated with the one or more fluids, applying a second pressure, distinct from the first applied pressure, to the exterior surface of a core sample, heating the core sample to an second elevated temperature distinct from the first elevated temperature, and generating NMR data of the core sample and the one or more fluids at the second applied pressure and second elevated temperature. In so doing, a second value for the one or more physical characteristics of the core sample and the one or more fluids is determined as a function of the second applied pressure and second elevated temperature. Such information can then be used to optimize an enhanced oil recovery process.

BRIEF DESCRIPTION OF THE DRAWINGS

Like reference numerals refer to corresponding parts throughout the drawings.

DESCRIPTION OF EMBODIMENTS

Figure 1A:
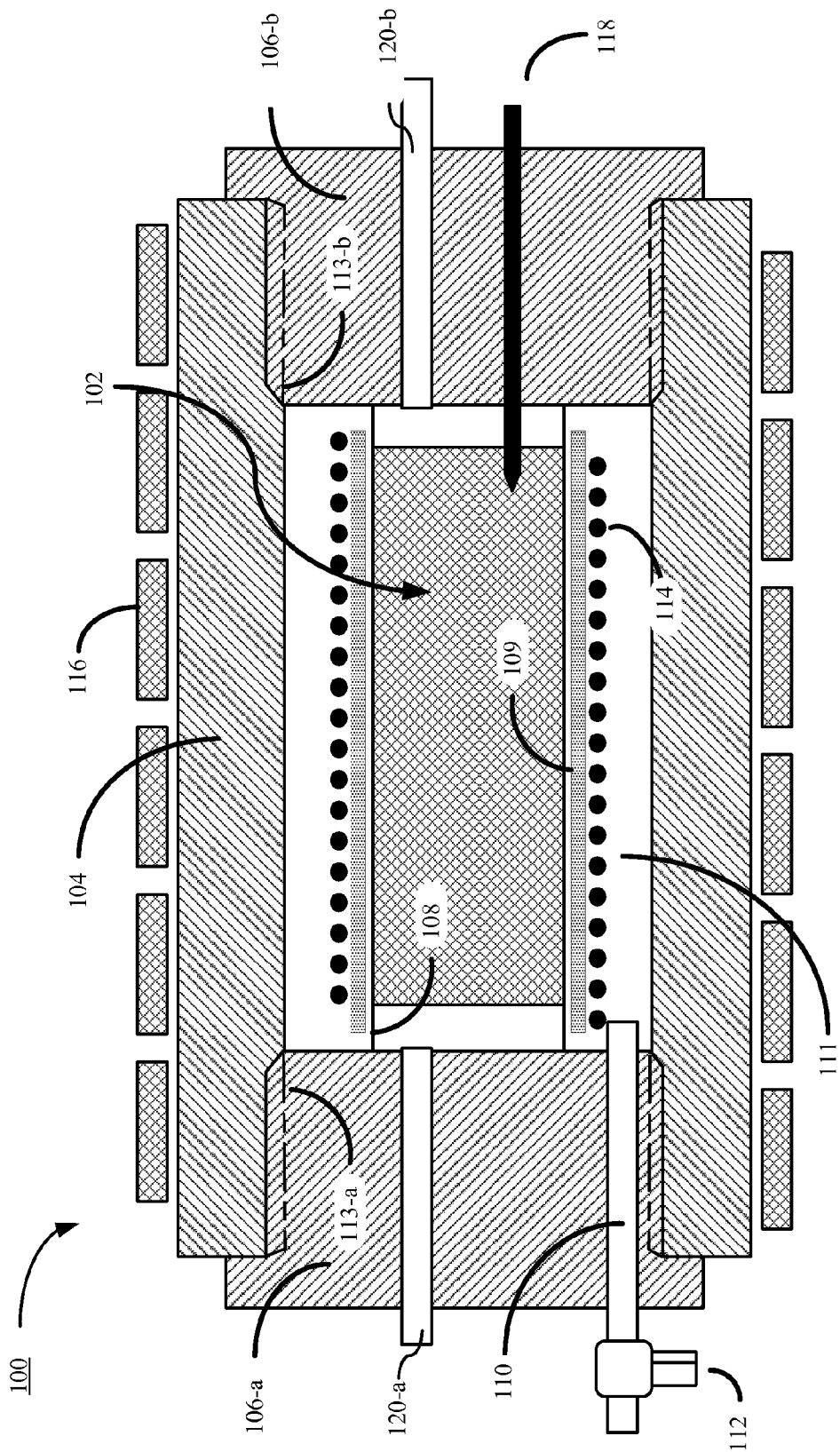
FIG. 1A is a schematic longitudinal sectional view of a core holder assembly in accordance with some embodiments.

It will be understood that, although the terms "first," "second," etc. are optionally used herein to describe various elements, these elements should not be limited by these terms. These terms are only used to distinguish one element from another. For example, a first element could be termed a second element, and, similarly, a second element could be termed a first element, without changing the meaning of the description, so long as all occurrences of the "first element" are renamed consistently and all occurrences of the second element are renamed consistently. The first element and the second element are both elements, but they are not the same element.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, operations, operations, elements, and/or components, but do not preclude the presence or addition of one or more other features, integers, operations, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

As used herein, the term "brine" may be construed to mean a fluid that includes various salts and salt mixtures dissolved in an aqueous solution, any saline fluid used in completion operations or pay zone penetrating operations, and/or any fluid used in an enhanced oil recovery processes. In some circumstances, brines have higher densities than fresh water but lack solid particles that might damage producible formations. Particular classes of brines include chloride brines (calcium and sodium), bromides and formates.

Reference will now be made in detail to various embodiments, examples of which are illustrated in the accompanying drawings. In the following detailed description, numerous specific details are set forth in order to provide a thorough understanding of the present disclosure and the described embodiments herein. However, embodiments described herein may be practiced without these specific details. In other instances, well-known methods, procedures, components, and mechanical apparatus have not been described in detail so as not to unnecessarily obscure aspects of the embodiments.

FIG. 1 depicts a core holder assembly 100, in accordance with some embodiments. During use, a core sample 102 taken from a hydrocarbon containing formation resides within the core holder assembly 100. In typical embodiments, core sample 102 generally is cylindrical. However, in other embodiments core sample 102 is any shape and size.

In some embodiments, the core holder assembly 100 includes a pressure chamber provided by a hull 104 and a pair of disk-shaped flanges 106-a and 106-b that are arranged at opposite sides of the hull 104. In some embodiments, the hull 104 is a tubular hull (e.g., is substantially cylindrical in cross-section). In some embodiments, the hull 104 comprises stainless steel, titanium, or some other metal, metal alloy, or combination thereof. In some embodiments, the disk-shaped flanges 106-a and 106-b comprise substantially the same material as the hull 104. In other embodiments, the disk-shaped flanges comprise a material distinct from the hull. In some embodiments, one of the disk-shaped flanges 106 is permanently affixed to the hull (e.g., by welding).

The core holder assembly 100 further includes a flexible core holder sleeve 108, which is arranged within the hull 104 and is sealingly coupled with the disk-shaped flanges 106. In some embodiments, the hull 104 is coupled to at least one of the disk-shape flanges 106-a and 106-b via threads 113-a and 113-b, respectively. In some embodiments, the disk-shaped flanges are sealingly coupled to the flexible core holder sleeve 108 by means of a gasket upon which pressure is applied using threads 113-a and 113-b. In some embodiments, the flexible core sample holder sleeve 108 comprises a non-magnetic plastic polymer. In some embodiments, the non-magnetic plastic is substantially free of hydrogen. In some embodiments, the flexible core sample holder sleeve 108 material comprises polytetrafluoroethylene. In some embodiments, a tubular supporter 109 surrounds the flexible core sample holder sleeve. In some embodiments, the tubular supporter comprises polyether ether ketone (PEEK).

The core holder assembly 100 further includes an overburden fluid injection port 110 fed through one of the disk-shaped flanges 106. In some circumstances, the overburden fluid injection port 110 is used for injecting overburden fluid into an annular space 111 between the hull 104 and the flexible core sample holder sleeve 108, thereby applying a pressure to the flexible core sample holder sleeve 108. In some embodiments, the tubular supporter 109 is disposed around the flexible core sample holder sleeve 108 in such a manner as to allow the flexible core holder sleeve 108 to remain immersed in the overburden fluid. In some embodiments, the flexible core sample holder sleeve 108 is designed to substantially transfer the applied pressure from an exterior surface of the flexible core sample holder sleeve 108 to an interior surface of flexible core sample holder sleeve 108, thereby applying a pressure to a core sample residing in the flexible core sample holder sleeve 108 during use.

The core holder assembly 100 further includes a pressure regulator 112 for maintaining the overburden fluid in the annular space at a predetermined gauge pressure (e.g., a pressure differential between the annular space and the ambient, atmospheric pressure of the laboratory). In some embodiments, the applied gauge pressure that the outer sleeve is capable of withstanding is a pressure in a range between 0 psig-10,000 psi, 0 psig-8,000 psi, 0 psig-7,500 psi, 0 psig-10,000 psi, or 0 psig to 7,500 psig.

The core holder assembly 100 further includes a radio-frequency (RF) antenna 114 within the pressure chamber. The radio-frequency (RF) antenna 114 is wrapped around the flexible core sample holder sleeve 108 (e.g., helically, or solenoidally). Alternatively, in some embodiments, the RF antenna 114 is wrapped around the tubular supporter. The RF antenna 114 is configured to receive an electromagnetic-signal, such as a NMR signal, from the core sample. In use, the core sample 102 is arranged substantially within the sleeve. In some embodiments, the core holder assembly 100 further includes one or more electrical feedthroughs configured to electrically couple a first terminal and a second terminal of the RF antenna to external circuitry.

In some embodiments, the core holder assembly 100 further includes one or more heating elements 116. In some embodiments, the one or more heating elements 116 are disposed on an outer surface of the pressure chamber. In FIG. 1, a single heating element 116 (e.g., a resistive heating element) is shown wrapped around an outer surface of hull (and thus is also disposed on the outer surface of the pressure chamber). In some embodiments, however, one or more heating elements are incorporated into the interior of the pressure chamber, for example, on an inside surface of the hull. The heating element 116 is configured to heat the overburden fluid, which acts as heat transfer medium thereby heating the core sample to an elevated temperature. In some embodiments, the elevated temperature is maintained by a temperature controller. In some embodiments, the heating element 116 is isolated from an outside environment by thermally insulating material to prevent heat generated by the heating element 116 from transferring to the outside environment. In some embodiments, the temperature controller is provided with one or more thermocouples 118 that are, optionally, fed through one of the disk-shaped flanges 106 and configured to be pierced into a tail end of the core sample. In other embodiments, a sensor end of a particular thermocouple 118 is disposed within the annular space such that it is immersed in overburden fluid. A suitable calibration scheme is then used so that the temperature regulator accurately maintains the temperature of the core sample. In some embodiments, the heating element is capable of heating the core sample to an elevated temperature in the range of about 200 degrees Fahrenheit to about 500 degrees Fahrenheit. In some embodiments, the heating element is capable of heating the core sample to an elevated temperature in the range of about room temperature to 350 degrees Fahrenheit.

In some embodiments, the core holder assembly 100 further includes a flooding fluid injection port 120-a fed through one of the flanges of the pair of flanges for injecting a flooding fluid into the core sample, and a fluid outlet port fed 120-b through the other flange for discharge of pore and/or injected fluid from the core sample. In some circumstances, the flooding fluid injection port 120-a and outlet port 120-b are for use in flooding experiments, which are described in more detail below with reference to method 200 and FIGS. 2A-2C.

Figure 1B:
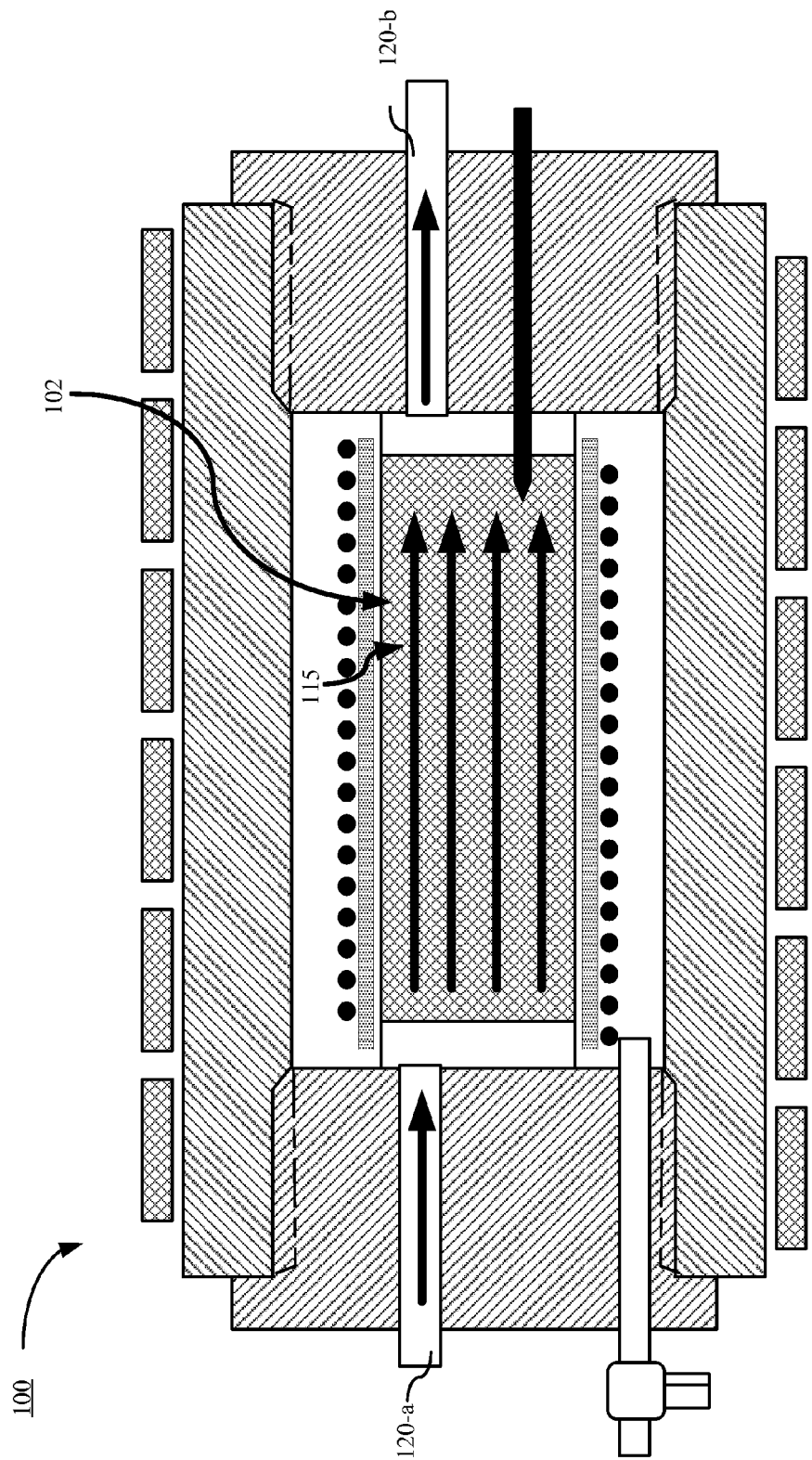
FIG. 1B is a schematic longitudinal sectional view of a core holder assembly showing an exemplary flow pattern in accordance with some embodiments.

An exemplary fluid flow pattern (e.g., of the flooding fluid injected into the core sample) is shown in FIG. 1B. FIG. 1B is otherwise analogous to FIG. 1A, with the exception that FIG. 1B includes flow lines 115 illustrating the exemplary flow pattern between fluid injection port 120-*a* and outlet port 120-*b*. In some circumstances, the flow pattern is non-uniform, depending upon the specifics of injection of the fluid through fluid injection port 120-*a*, outlet through outlet port 120-*b*, the nature of the rock (e.g., spatial variations in permeability, etc). In some embodiments, a flow rate of the flow pattern is approximately constant. Alternatively, various flow rates are used. In some embodiments, an alternating flow gradient is employed during flooding. It should be understood that the range of flow range can be wide as long as the pressure caused by the flooding process is within the designed pressure limit of the core holder assembly 100.

Accordingly, the core holder assembly 100 allows flooding experiments to be performed under realistic high-pressure, high temperature (HPHT) well (e.g., logging) conditions while using the RF antenna 114 to measure NMR signals.

The core holder assembly 100 may be used for static or core flooding experiments for the experimental study of process parameters for enhanced oil recovery (EOR) processes, described with reference to method 200 and FIGS. 2A-2C, below. For example, these process parameters may play a role during steam injection processes for thermal EOR of heavy oil (HVO) fields. In such a circumstance, one objective is to shed light on the fundamentals of heat transfer and oil mobilization prevailing during steam flooding and cyclic steam stimulation, and to optimize the process parameters for EOR.

Figure 2A:
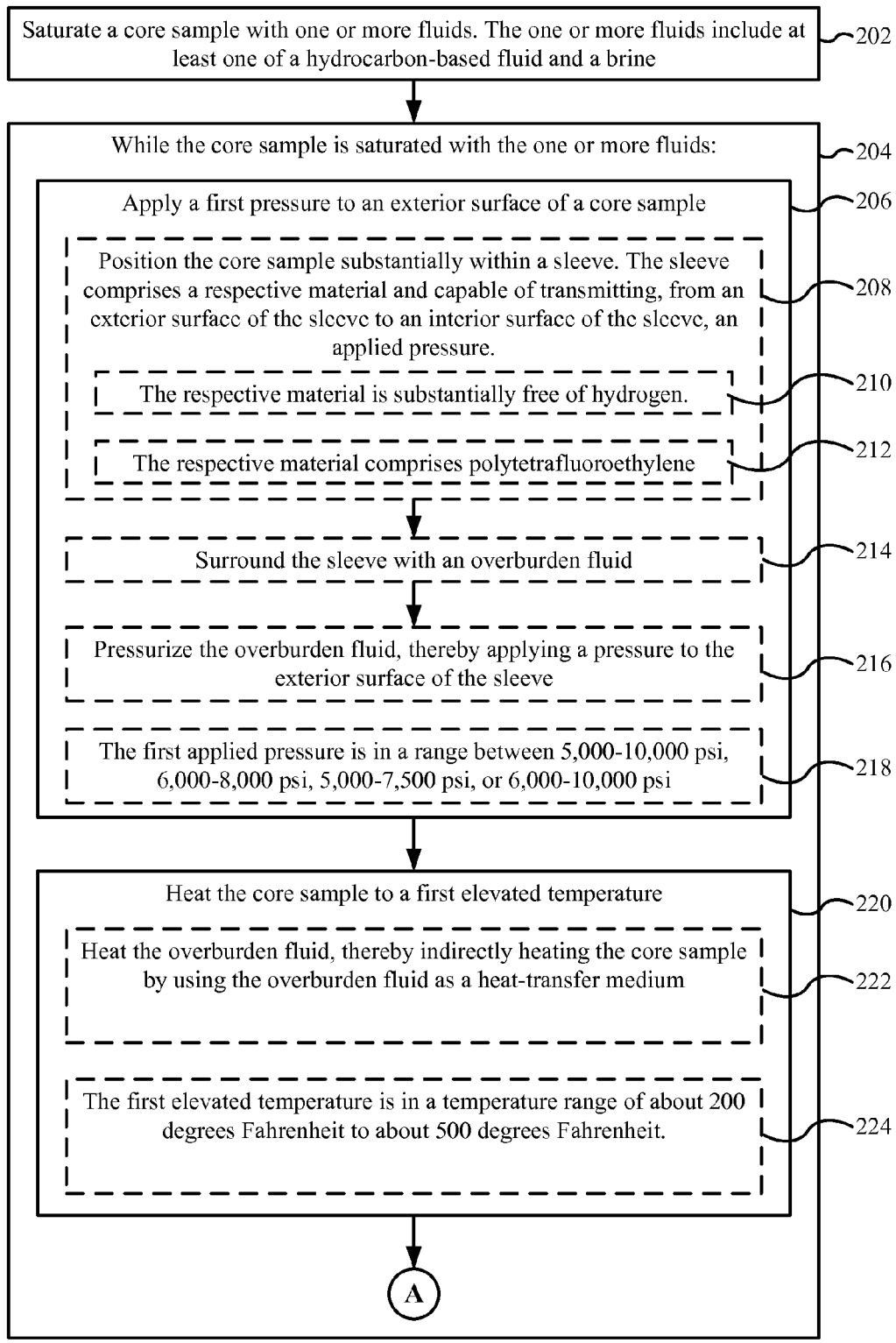
FIGS. 2A-2C are flow charts illustrating a method of performing a laboratory nuclear magnetic resonance measurements of a core sample, in accordance with some embodiments.
Figure 2B:
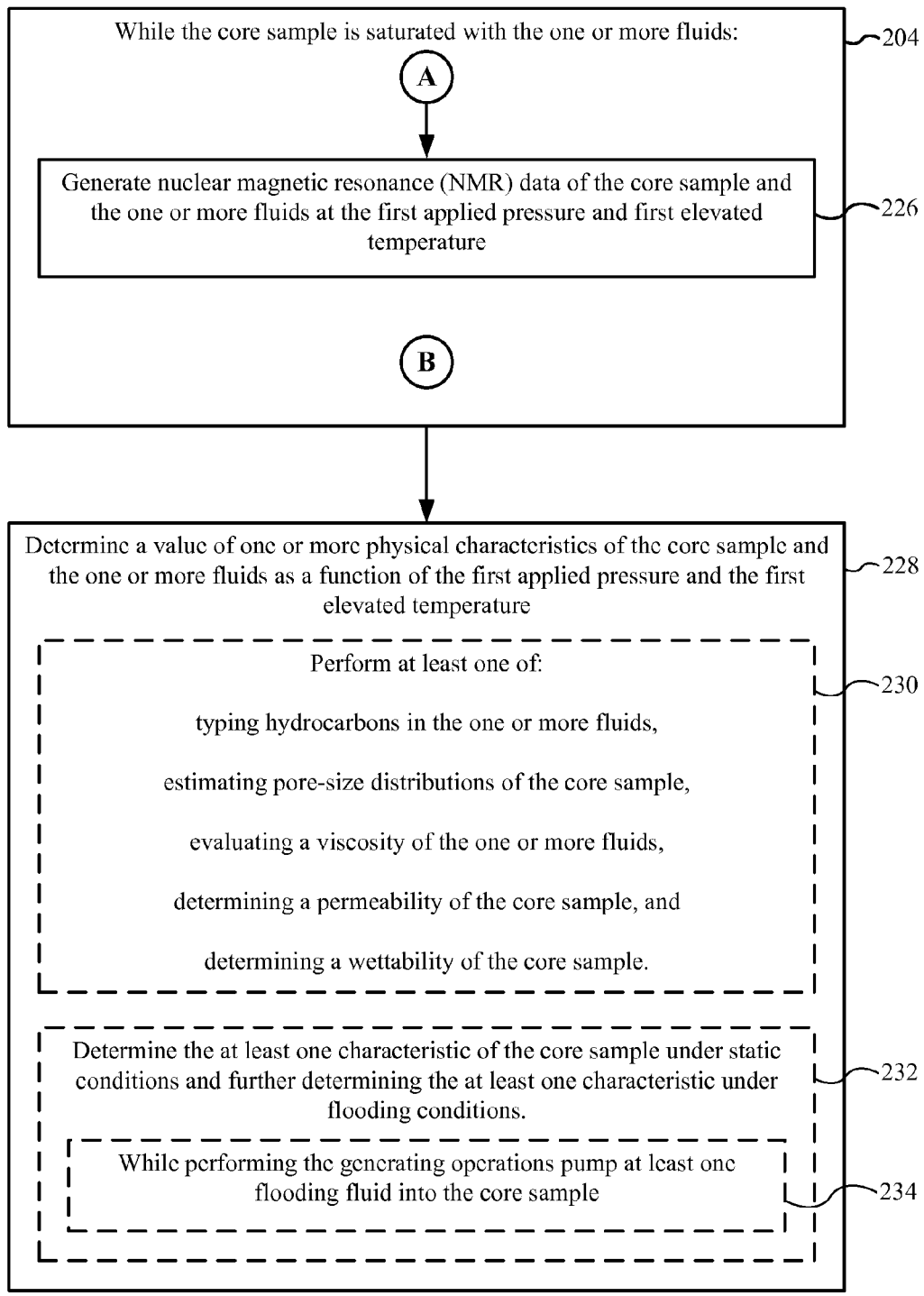
Figure 2C:
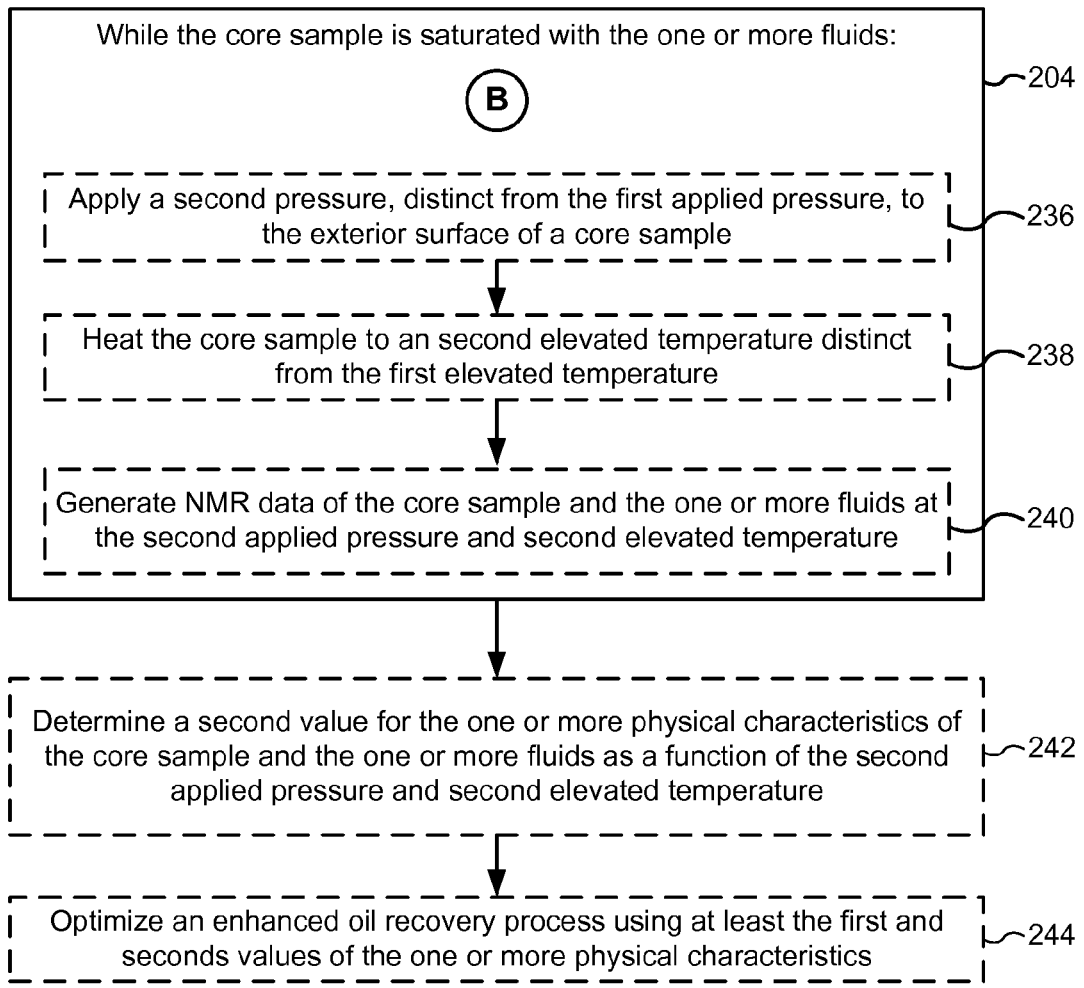

Accordingly, FIGS. 2A-2C are flowcharts illustrating a method 200 of performing laboratory nuclear magnetic resonance measurements of a core sample, in accordance with some embodiments using core holder assembly 100.

The method 200 includes saturating (202) a core sample with one or more fluids. The one or more fluids include at least one of a hydrocarbon-based fluid (e.g., oil) and a brine. For example, when the core sample is positioned within the flexible core sample holder sleeve 108 (FIG. 1), the one or more fluids can be pumped into flooding fluid injection port 120-*a* at a suitable pressure and for a suitable duration of time to saturate the core sample with the one or more fluids.

The method 200 further includes, while the core sample is (204) saturated with the one or more fluids, applying (206) a first pressure to an exterior surface of a core sample. In some embodiments, applying the first pressure to the sleeve includes positioning (208) the core sample substantially within a sleeve (e.g., the flexible core sample holder sleeve 108, FIG. 1). The sleeve comprises a respective material and is capable of transmitting, from an exterior surface of the sleeve to an interior surface of the sleeve, an applied pressure. Thus, when a pressure is applied to the exterior surface of the sleeve, the pressure is substantially transmitted to the core sample substantially within the sleeve. In some embodiments, the respective material is (210) substantially free of hydrogen. Using a material that is substantially free of hydrogen for the sleeve allows for the use of hydrogen-based NMR experiments, which would otherwise be hindered by a detrimental hydrogen NMR signal of the sleeve. In some embodiments, the respective material comprises polytetrafluoroethylene (212), which is known by the trade name TEFLON®, produced the DuPont Corporation. Polytetrafluoroethylene is capable of withstanding a variety of temperatures and pressures of interest when performing laboratory NMR experiments of core samples under conditions representative of in-situ conditions.

In some embodiments, applying the first pressure further includes surrounding (214) the sleeve with an overburden fluid (e.g., by injecting the overburden fluid into the annular space via overburden fluid injection port 110, FIG. 1). In some embodiments, the overburden fluid is substantially free of hydrogen. In some embodiments, the overburden fluid is electrically insulating. In some embodiments, the overburden fluid comprises a fluorocarbon-based fluid. In some embodiments, the overburden fluid comprises a fluid having a chemical formula $C_xF_y$, where x and y are the same or different positive integers. In some embodiments, the overburden fluid comprises one or more FLUORINERT™ fluids (e.g., FC-70, FC-75) produced by the 3M Corporation.

In some embodiments, applying the first pressure further includes pressurizing (216) the overburden fluid (e.g., using pressure regulator 112, FIG. 1), thereby applying a pressure to the exterior surface of the sleeve. In some embodiments, the first applied pressure is (218) in a range between 0 psig to 7,500 psig.

The method 200 further includes, while the core sample is saturated with the one or more fluids, heating (220) the core sample to a first elevated temperature. In some embodiments, heating the core sample includes heating (222) the overburden fluid, thereby indirectly heating the core sample by using the overburden fluid as a heat-transfer medium. For example, a heating element (e.g., heating element 116, FIG. 1) can be disposed inside or outside of a pressure chamber containing the overburden fluid. Heat from the heating element is transferred to the overburden fluid, and subsequently to the core sample. In some embodiments, the first elevated temperature is (224) in a temperature range of about 200 degrees Fahrenheit to about 500 degrees Fahrenheit. In some embodiments, the temperature is monitored by a thermocouple disposed either in the core sample, on the exterior surface of pressure chamber or in the overburden fluid, as described with reference to FIG. 1.

The method 200 further includes, while the core sample is saturated with the one or more fluids, generating (226) NMR data of the core sample and the one or more fluids at the first applied pressure and first elevated temperature (e.g., using RF antenna 114 to receive an NMR signal from the core sample). In some embodiments, the NMR data is low-field NMR data taken while the core sample is subject to a uniform low magnetic field (e.g., in the range of mT, µT, or nT). In some embodiments, the low magnetic field is the Earth's magnetic field.

The method 200 further includes determining (228) a value of one or more physical characteristics of the core sample and the one or more fluids as a function of the first applied pressure and the first elevated temperature. In some embodiments, determining the value of the one or more physical characteristics of includes performing (230) at least one of: typing hydrocarbons in the one or more fluids, estimating pore-size distributions of the core sample, evaluating a viscosity of the one or more fluids, determining a permeability of the core sample, and determining a wettability of the core sample. It is envisioned that the operation of determining the one or more physical characteristics could take place in real-time (e.g., while the core sample is saturated with the one or more fluids), or during off-line analysis, or a combination thereof.

In some embodiments, the method 200 further includes determining (232) the at least one characteristic of the core sample under static conditions and further determining the at least one characteristic under flooding conditions. In some embodiments, determining the at least one characteristic under flooding conditions includes, while performing the generating operation, pumping (234) at least one flooding fluid into the core sample. In some embodiments, the at least one flooding fluid is pumped into the core sample at a substantially constant rate. In some embodiments, the at least one flooding fluid includes oil, water, brine, or a mixture thereof. In some embodiments, the at least one flooding fluid includes a gas. In some embodiments, the gas includes carbon dioxide, nitrogen, methane, sulfur dioxide, nitrogen dioxide, or a mixture thereof.

In some embodiments, the method 200 further includes, while the core sample is saturated with the one or more fluids, applying (236) a second pressure, distinct from the first applied pressure, to the exterior surface of a core sample, heating (238) the core sample to a second elevated temperature distinct from the first elevated temperature, and generating (240) NMR data of the core sample and the one or more fluids at the second applied pressure and second elevated temperature.

In some embodiments, the method 200 further includes determining (242) a second value for the one or more physical characteristics of the core sample and the one or more fluids as a function of the second applied pressure and second elevated temperature. It is further envisioned that the first and second values could each be determined under each of static and flooding conditionings using the procedure described above.

In some embodiments, the method 200 further includes optimizing (244) an enhanced oil recovery process using at least the first and seconds values (e.g., under static conditions, flooding conditions, or a combination thereof) of the one or more physical characteristics.

FIGS. 3A-3E are graphical representations of exemplary data illustrating wettability variation with temperature of a particular hydrocarbon containing or other formation using 2D NMR, in accordance with some embodiments. Data presented in FIGS. 3A-3E are obtained, for example, by practicing aspects of method 200 described with reference to FIG. 2A-2C.

Figure 3A:
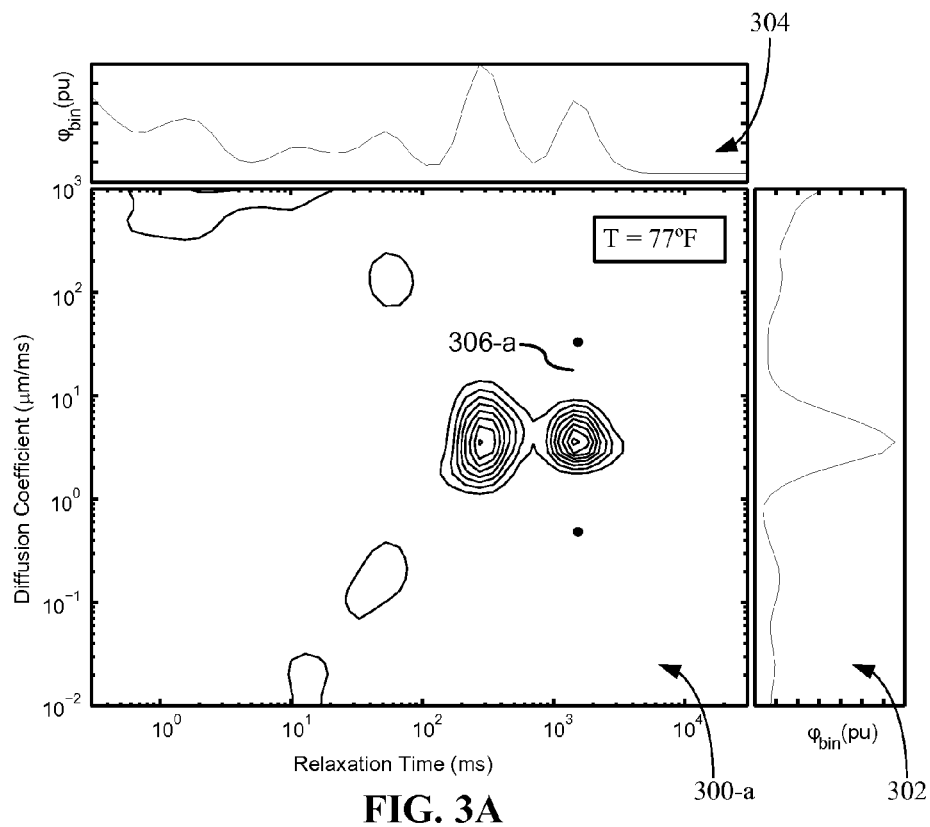
FIGS. 3A-3E are graphical representations of exemplary data illustrating wettability variation with temperature of a particular hydrocarbon containing or other formation using 2D NMR, in accordance with some embodiments.

FIG. 3A includes plot 300, which is a 2D NMR contour plot illustrating NMR signal strength (represented by contours) versus a $T_2$ relaxation time in milliseconds (labeled "Relaxation Time (ms)") along the horizontal axis and a diffusion coefficient in micrometers per millisecond along the vertical axis. Plot 300 corresponds to a respective hydrocarbon containing or other formation (e.g., data is obtained using a core-sample taken therefrom) at a pressure of about 2,000 psig and a temperature of 77 degrees Fahrenheit. FIG. 3A also includes plot 302, which is a one-dimensional plot of NMR signal strength versus diffusion coefficient (i.e., averaged over the $T_2$ relaxation time) and plot 304, which is a one-dimensional plot of NMR signal strength versus $T_2$ relaxation time (i.e., averaged over the diffusion coefficient). Plot 300 shows a peak in the NMR signal due water at a location designated by 306-a, indicating an apparent $T_2$ relaxation time of water ($T_{2a,w}$).

Figure 3B:
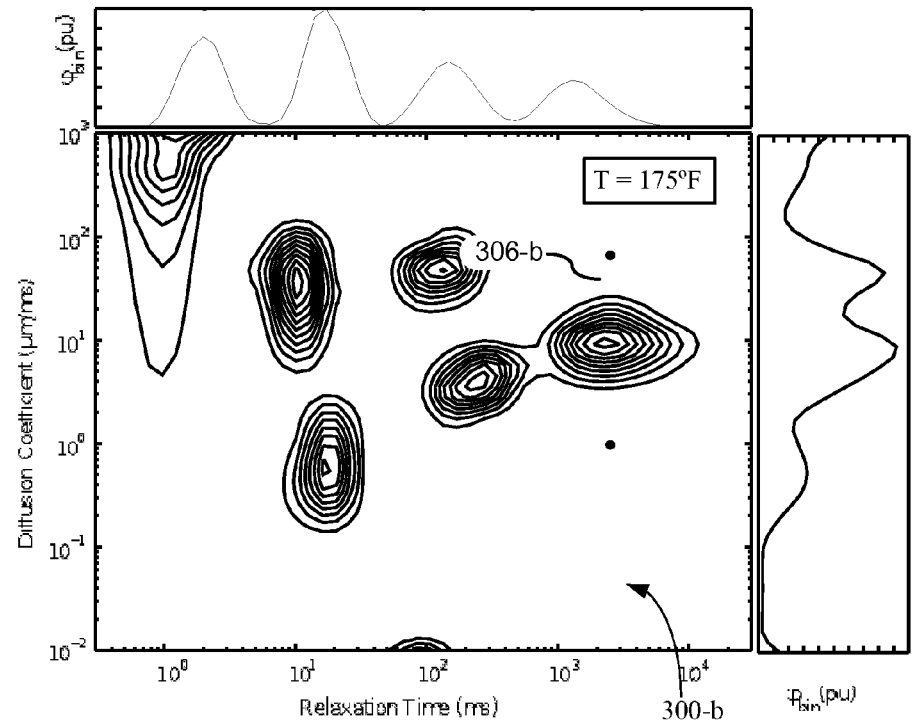

FIG. 3B is analogous to FIG. 3A with the difference being that data shown in FIG. 3B is taken at a pressure of about 2,000 psig and an elevated temperature of 175 degrees Fahrenheit. Plot 300-b again shows the water peak in the NMR signal, however, in plot 300-b, the location of the water peak has moved slightly to the right along the horizontal axis to a location designated by 306-b. The movement of the location of the water peak to the right in plot 300 signifies a water wet condition of the core-sample's water peak, which represents a condition of the core-sample in which a thin film of water coats a surface of a matrix of the core-sample and thus the formation rock preferentially imbibes water. Such a water wet condition is desirable for efficient oil transport and is thus desirable for enhanced oil recovery.

Figure 3C:
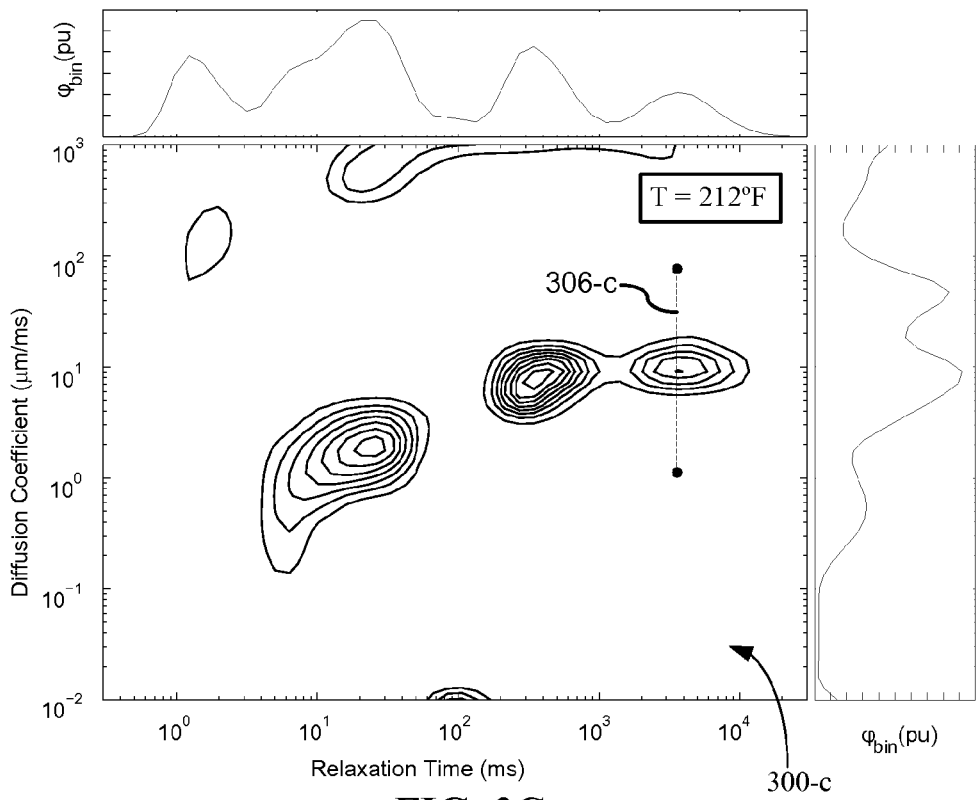

FIG. 3C is analogous to FIG. 3B with the difference that data shown in FIG. 3C is taken at a pressure of about 2,000 psig and an elevated temperature of 212 degrees Fahrenheit. Plot 300-c again shows the water peak in the NMR signal, however, in plot 300-c, the location of the water peak has moved further to the right of 306-b along the horizontal axis to a location designated by 306-c. As described below, in this exemplary data, temperatures higher than 212 degrees cause the water peak to transition to an oil wet condition (e.g., the water peak is characterized by a "kink-point" at 212 degrees), which is not desirable for enhanced oil recovery. An optimum (e.g., highest) diffusion coefficient under water wet conditions is also observed when the temperature is 212 degrees.

Figure 3D:
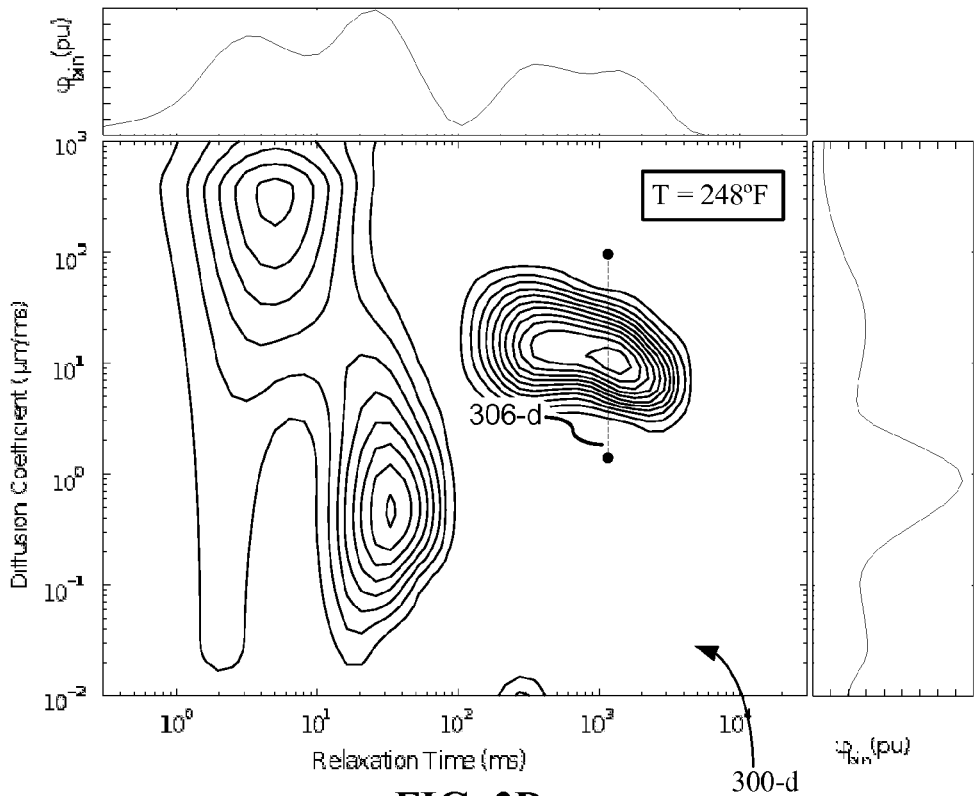

FIG. 3D is analogous to FIG. 3C with the difference being that data shown in FIG. 3D is taken at a pressure of about 2,000 psig and an elevated temperature of 248 degrees Fahrenheit. Plot 300-d again shows the water peak in the NMR signal, however, in plot 300-d, the location of the water peak has moved to the left of 306-c along the horizontal axis to a location designated by 306-d. The movement of the location of the water peak to the left in plot 300-d signifies an oil wet condition of the core-sample's water peak, which represents a condition of the core-sample in which a thin film of oil coats the surface matrix of the core-sample and thus the formation rock preferentially imbibes oil. Such an oil wet condition is detrimental for efficient oil transport and recovery and is thus not desirable for enhanced oil recovery.

Figure 3E:
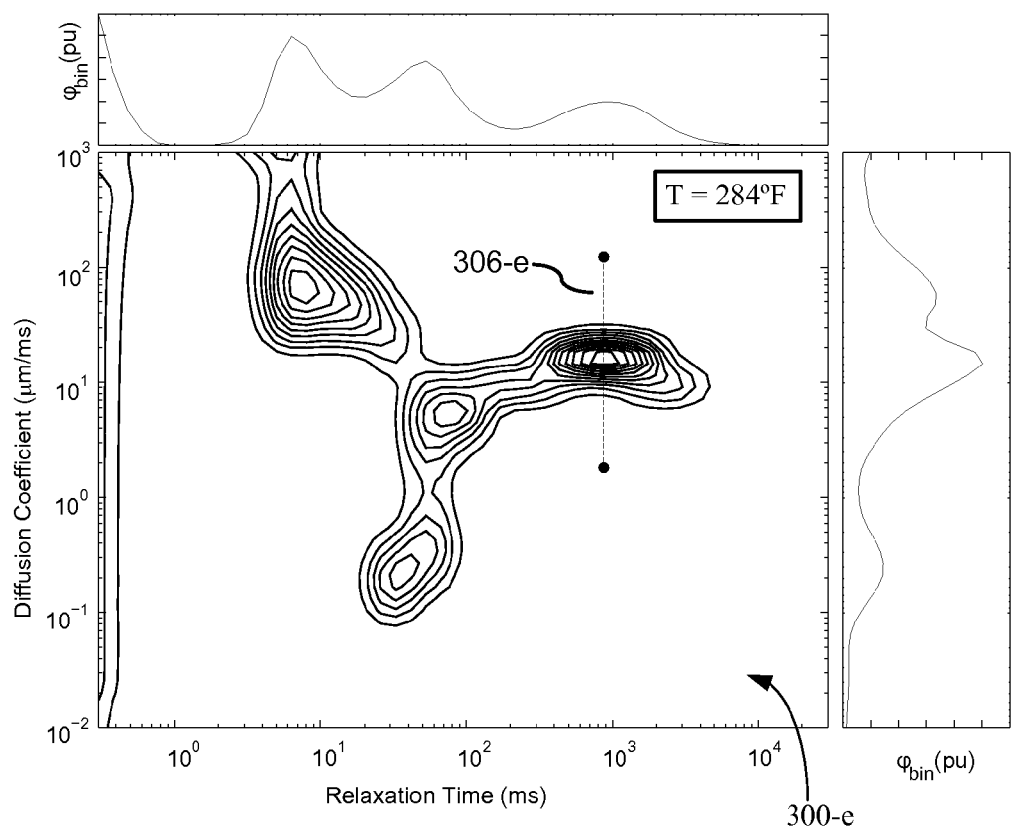

FIG. 3E is analogous to FIG. 3D with the difference being that data shown in FIG. 3E is taken at a pressure of about 2,000 psig and an elevated temperature of 284 degrees Fahrenheit. Plot 300-e again shows the water peak in the NMR signal, however, in plot 300-e, the location of the water peak has moved further to the left of 306-d along the horizontal axis to a location designated by 306-d, signifying that the water peak remains in the oil wet condition.

In some embodiments, the peak locations 306 are used to generate a forward model of one or more wettability indices of the core sample (e.g., a water index and an oil index), as described below. In some embodiments, because the core sample is taken from a respective hydrocarbon or other containing formation, the forward model for the one or more indices of the core sample is also a forward model for the one or more indices of the respective hydrocarbon or other containing formation.

The apparent $T_2$ relaxation time of water ($T_{2a,w}$) at a given temperature is related to the water wettability index via the equation:

$$\frac{1}{T_{2a,w}} = \frac{1}{T_{2b,w}} + \frac{I_{wA}+1}{2S_w}\left(\frac{1}{T_{2a,w,(S_w=1)}} - \frac{1}{T_{2b,w}}\right) \qquad (1)$$

where $T_{2b,w}$ is a bulk $T_2$ relaxation time of water, $I_{wA}$ is a water wettability index (e.g., an Amott water wettability index), $S_w$ is a water saturation of pore spaces within the core sample (typically obtained through separate testing of a core sample from the same hydrocarbon or other containing formation), and $T_{2a,w,(Sw=1)}$ is an apparent $T_2$ relaxation time of water at $S_w=1$ when the pores spaces are strong water wet.

In general, $T_{2a,w}$, $T_{2b,w}$, and $I_{wA}$ are each a function of temperature. Thus, Eq. (1) is an implicit function of temperature. In some embodiments, the apparent $T_2$ relaxation time of water ($T_{2a,w}$) is measured at a variety of temperatures in a manner consistent with the method 200 and FIGS. 3A-3D, as described above, thereby providing an empirical relationship for $T_{2a,w}$ to use in conjunction with Eq. (1). In some embodiments, a relationship for a $T_1$ value of bulk water ($T_{1b,w}$) as a function of temperature is obtained by fitting empirical data with a function of the form:

$$T_{1b,w} = At^3 + Bt^2 + Ct + D \quad (2)$$

where t is the temperature of the bulk water. Such empirical data is provided, for example, in "Kleinberg, R. L., Vinegar, H. J., (1996) NMR properties of reservoir fluids. The Log Analyst 37(6), page 20-32," which is herein incorporated by reference in its entirety. A constant ratio of $T_{1b,w}/T_{2a,w}$ (e.g., constant as a function of temperature) is used to convert the $T_1$ values obtained from Eq. (2) into $T_2$ values. In some embodiments, the constant ratio is a fitting parameter. In some embodiments, the constant ratio is 2.5. Substituting the $T_{2a,w}$ obtained in this manner from Eq. (2) into Eq. (1), while using experimental data for $S_w$, and using the emperical relationship for $T_{2a,w}$ as a function of temperature yields an empirical relationship for $I_{wA}$ as a function of temperature. The empirical relationship is then converted to a forward model by fitting the empirical data to the equation:

$$I_{wA} = \frac{b_1 - b_2}{1 + (t/t_c)^\beta} + b_2, \quad (3)$$

where $b_1=0$, $b_2=1$, and $t_c$ and $\beta$ are fitting parameters for the forward model.

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings. The embodiments were chosen and described in order to best explain the principles of the disclosure and its practical applications, to thereby enable others skilled in the art to best utilize the various embodiments with various modifications as are suited to the particular use contemplated.

What is claimed:

1. A core sample holder assembly for performing a laboratory nuclear magnetic resonance measurement of a core sample taken from a hydrocarbon containing formation, comprising:
   a pressure chamber provided by a hull, and one or more flanges are sealingly coupled with the hull;
   a flexible core sample holder sleeve, the sleeve being disposed within the pressure chamber and sealingly coupled with at least one of the flanges;
   an overburden fluid injection port for injecting overburden fluid, the overburden fluid injection port in fluid communication with an annular space between the hull and the flexible sleeve;
   a pressure regulator for maintaining the overburden fluid in the annular space at a predetermined gauge pressure;
   a radio-frequency (RF) antenna within the pressure chamber and wrapped around the sample holder sleeve, wherein the RF antenna is configured to receive an electromagnetic-signal from the core sample, which in use is arranged substantially within the sleeve.

2. The apparatus of claim 1, further comprising at least one flange sealingly coupled at each end of the hull.

3. The apparatus of claim 1, further comprising a heating element disposed on an outer surface of the pressure chamber.

4. The apparatus of claim 3, wherein the heating element is configured to heat the core sample to an elevated temperature in the range of about 200 degrees Fahrenheit to about 500 degrees Fahrenheit.

5. The apparatus of claim 3, further comprising a thermocouple that is configured to monitor the elevated temperature of the core sample.

6. The apparatus of claim 1, further comprising:
   a flooding fluid injection port fed through one of the flanges of the pair of flanges, the flooding fluid injection port being configured to inject a flooding fluid into the core sample; and
   a fluid outlet port fed through the other flange of the pair of flanges, the fluid outlet port being configured for discharge of pore and/or injected fluid from the core sample.

7. The apparatus of claim 1, further comprising one or more electrical feedthroughs configured to electrically couple a first terminal and a second terminal of the RF antenna to external circuitry.

8. The apparatus of claim 1, wherein the applied gauge pressure that the outer sleeve is capable of withstanding is a pressure in a range between 0 psig to 7,500 psig.

9. The apparatus of claim 1, wherein the hull comprises stainless steel or titanium.

10. The apparatus of claim 1, wherein the flexible core sample holder sleeve comprises a non-magnetic plastic polymer.

11. The apparatus of claim 10, wherein the non-magnetic plastic is substantially free of hydrogen.

12. The apparatus of claim 1, wherein the flexible core sample holder sleeve comprises polytetrafluoroethylene.

13. The apparatus of claim 1, wherein the overburden fluid injection port for injecting overburden fluid is fed through one of the flanges into the annular space between the hull and the flexible sleeve.

14. A method of performing a laboratory nuclear magnetic resonance measurement of a core sample, comprising:
   saturating the core sample with one or more fluids;
   while the core sample is saturated with the one or more fluids:
      applying a first pressure to an exterior surface of a core sample;
      heating the core sample to a first elevated temperature;
      generating nuclear magnetic resonance (NMR) data of the core sample and the one or more fluids at the first applied pressure and first elevated temperature; and
      determining a value of one or more physical characteristics of the core sample and the one or more fluids as a function of the first applied pressure and the first elevated temperature.

15. The method of claim 14, wherein the one or more fluids comprising at least one of a hydrocarbon-based fluid and a brine.

16. The method of claim 14, wherein the first elevated temperature is in a temperature range of about 200 degrees Fahrenheit to about 500 degrees Fahrenheit.

17. The method of claim 14, wherein the first applied pressure is in a range between 5,000-10,000 psi.

18. The method of claim 14, wherein applying the pressure further comprises:
  positioning the core sample substantially within a sleeve, wherein the sleeve comprises a respective material and wherein the sleeve is capable of transmitting, from an exterior surface of the sleeve to an interior surface of the sleeve, an applied pressure;
  surrounding the sleeve with an overburden fluid; and
  pressurizing the overburden fluid, thereby applying a pressure to the exterior surface of the sleeve.

19. The method of claim 18, wherein heating the core sample to the first elevated temperature further comprises heating the overburden fluid, thereby indirectly heating the core sample by using the overburden fluid as a heat-transfer medium.

20. The method of claim 18, wherein the respective material comprises polytetrafluoroethylene.

21. The method of claim 18, wherein the respective material is substantially free of hydrogen.

22. The method of claim 18, wherein the overburden fluid is substantially free of hydrogen.

23. The method of claim 18, wherein the overburden fluid is electrically insulating.

24. The method of claim 18, wherein the overburden fluid comprises a fluorocarbon-based fluid.

25. The method of claim 24, wherein the overburden fluid comprises a fluid having a chemical formula $C_xF_y$.

26. The method of claim 14, wherein determining one or more physical characteristics of the core sample includes performing at least one of:
  typing hydrocarbons in the one or more fluids;
  estimating pore-size distributions of the core sample;
  evaluating a viscosity of the one or more fluids;
  determining a permeability of the core sample;
  determining a wettability of the core sample; and
  determining an oil/brine saturation of the core sample.

27. The method of claim 14, further comprising, generating a forward model for one or more wettability indices of the core sample.

28. The method of claim 14, further comprising, determining the at least one characteristic of the core sample under static conditions and further determining the at least one characteristic under flooding conditions.

29. The method of claim 28, wherein determining at least one characteristic under flooding conditions further includes, while performing the generating operation, pumping at least one flooding fluid into the core sample.

30. The method of claim 29, wherein the at least one flooding fluid is pumped into the core sample at a substantially constant rate.

31. The method of claim 29, wherein the at least one flooding fluid includes oil, water, brine, or a mixture thereof.

32. The method of claim 29, wherein the at least one flooding fluid includes a gas.

33. The method of claim 32, wherein the gas includes carbon dioxide, nitrogen, methane, sulfur dioxide, nitrogen dioxide, or a mixture thereof.

34. The method of claim 14, further comprising,
  while the core sample is saturated with the one or more fluids:
    applying a second pressure, distinct from the first applied pressure, to the exterior surface of a core sample;
    heating the core sample to an second elevated temperature distinct from the first elevated temperature;
    generating NMR data of the core sample and the one or more fluids at the second applied pressure and second elevated temperature; and
  determining a second value for the one or more physical characteristics of the core sample and the one or more fluids as a function of the second applied pressure and second elevated temperature.

35. The method of claim 34, further comprising optimizing an enhanced oil recovery process using at least the first and second values of the one or more physical characteristics.

* * * * *